United States Patent
Tian et al.

(10) Patent No.: US 11,779,237 B2
(45) Date of Patent: Oct. 10, 2023

(54) HYSTERESIS EFFECT-BASED FIELD FREE POINT-MAGNETIC PARTICLE IMAGING METHOD

(71) Applicant: Beijing University of Aeronautics and Astronautics, Beijing (CN)

(72) Inventors: Jie Tian, Beijing (CN); Yimeng Li, Beijing (CN); Yu An, Beijing (CN); Jing Zhong, Beijing (CN); Jie He, Beijing (CN); Bo Zhang, Beijing (CN)

(73) Assignee: Beihang University

( * ) Notice: Subject to any disclaimer, the term of this patent is extended or adjusted under 35 U.S.C. 154(b) by 0 days.

(21) Appl. No.: 17/828,026

(22) Filed: May 30, 2022

(65) Prior Publication Data
US 2023/0024179 A1    Jan. 26, 2023

(51) Int. Cl.
*A61B 5/0515* (2021.01)
*G01R 33/12* (2006.01)
*G01R 33/14* (2006.01)
*G01R 33/24* (2006.01)

(52) U.S. Cl.
CPC ........ *A61B 5/0515* (2013.01); *G01R 33/1276* (2013.01); *G01R 33/14* (2013.01); *G01R 33/24* (2013.01)

(58) Field of Classification Search
CPC .. A61B 5/0515; G01R 33/1276; G01R 33/14; G01R 33/24
See application file for complete search history.

(56) References Cited

U.S. PATENT DOCUMENTS

| 2011/0221438 A1* | 9/2011 | Goodwill | A61B 5/0515 324/301 |
| 2022/0260655 A1* | 8/2022 | Conolly | G01R 33/1276 |

FOREIGN PATENT DOCUMENTS

| WO | WO-2011116229 A2 * | 9/2011 | A61B 5/05 |
| WO | WO 2021/016473 * | 1/2021 | A61B 5/0515 |

OTHER PUBLICATIONS

Ferguson et al. "Tailoring the magnetic and pharmacokinetic properties of iron oxide magnetic particle imaging tracers." Biomed Tech (Berl). Dec. 2013; 58(6): 493-507.*
(Continued)

*Primary Examiner* — Joel Lamprecht
*Assistant Examiner* — Nyrobi Celestine

(57) ABSTRACT

A hysteresis effect-based Field Free Point-Magnetic Particle Imaging (FFP-MPI) method includes the following steps: acquiring a hysteresis loop model of Superparamagnetic Iron Oxide Nanoparticles (SPIOs); calculating to obtain a Point Spread Function (PSF) of the SPIOs on the basis of a sinusoidal excitation magnetic field and the hysteresis loop model of the SPIOs; acquiring an original reconstructed image of FFP-MPI on the basis an FFP moving track and a voltage signal; performing deconvolution on the original image with respect to the PSF considering an hysteresis effect, so as to obtain a final reconstructed image; the artifacts and phase errors of image reconstruction caused by the hysteresis effect of the SPIOs with large particle sizes are reduced, the deficiency in reconstruction by the traditional reconstruction method that ignores the hysteresis effect is overcome, the reconstruction speed and the resolution are greatly improved, and the application range of the SPIOs is expanded.

2 Claims, 6 Drawing Sheets

(56) References Cited

OTHER PUBLICATIONS

Carrey et al. "Simple models for dynamic hysteresis loop calculations of magnetic single domain nanoparticles: application to magnetic hyperthermia optimization." J Appl Phys. 2011; 109:083921.*

Goodwill et al. "Multidimensional X-Space Magnetic Particle Imaging." IEEE Trans Med Imaging. Sep. 2011 ; 30(9): 1581-1590.*

J. Rahmer et al, "First experimental evidence of the feasibility of multi-color magnetic particle imaging", Physics in Medicine and Biology, vol. 60, pp. 1775-1791, Feb. 2015 (Year: 2015).*

R. D. Dhavalikar, "Modeling the Response of Magnetic Nanoparticles to Magnetic Fields in Magnetic Particle Imaging", University of Florida, Dissertation, pp. 1-137, 2017 (Year: 2017).*

M. M. van de Loosdrecht et al, "A novel characterization technique for superparamagnetic iron oxide nanoparticles: The superparamagnetic quantifier, compared with magnetic particle spectroscopy", Review of Scientific Instruments, vol. 90, No. 024101, p. 1-9, Feb. 2019 (Year: 2019).*

C. Shasha et al, "Discriminating nanoparticle core size using multi-contrast MPI", Physics in Medicine and Biology, vol. 64, pp. 1-11, Mar. 2019 (Year: 2019).*

* cited by examiner

HYSTERESIS EFFECT-BASED FIELD FREE POINT-MAGNETIC PARTICLE IMAGING METHOD

TECHNICAL FIELD

The present invention relates to the field of magnetic nanoparticle imaging, and particularly relates to a hysteresis effect-based Field Free Point-Magnetic Particle Imaging (FFP-MPI) method.

BACKGROUND

MPI is a novel imaging method. A Field Free Point (FFP) or a Field Free Line (FFL) is constructed, so that Superparamagnetic Iron Oxide Nanoparticles (SPIOs) in an FFP or FFL area generate a response to an excitation magnetic field, while the SPIOs in other areas are in a magnetic saturation state and do not have a response to the excitation magnetic field, and the purpose of performing spatial coding reconstruction on magnetic particle distribution information is achieved, thereby performing precise positioning on a detection object, such as a tumor. The MPI has the characteristics of high time resolution, high spatial resolution, and no harmful radiation, so it has a very good application prospect in the field of medicine.

At present, image reconstruction theoretical methods of the MPI are all based on Langevin function. It is considered that magnetic particles are adiabatically aligned with an externally applied excitation magnetic field, so as not to produce a hysteresis effect. However, when the particle sizes of the SPIOs in actual application are less than 14 nm, the hysteresis effect of the particles is very low and can be ignored; but when the particle sizes are greater than 14 nm, the hysteresis effect of the particles is obvious. The basic assumptions of a Langevin magnetization curve-based image reconstruction algorithm are no longer satisfied, and artifacts and deviations appear in a constructed image. Most SPIOs used for biomedical MPI at present are about 20 nm, so the hysteresis effect cannot be ignored. Therefore, an image reconstruction algorithm considering the hysteresis effect of the magnetic particles is needed.

SUMMARY

In order to solve artifacts of a reconstructed image caused by a hysteresis effect of SPIOs in the prior art, the present disclosure provides a hysteresis effect-based FFP-MPI method. Starting from constructing a hysteresis loop model of the SPIOs, the variations of the characteristics of a Point Spread Function (PSF) are analyzed on the basis of the hysteresis effect, a voltage signal received by an induction coil is reconstructed according to a scanning track of an FFP-MPI system to obtain an original reconstructed image, and finally, deconvolution is performed according to the PSF of the hysteresis effect, so as to obtain a high-quality final reconstructed image. Specific technical solutions are as follows.

A hysteresis effect-based FFP-MPI method includes the following steps:

S1: acquiring a hysteresis loop model of the SPIOs;
S2: calculating to obtain a PSF of the SPIOs on the basis of a sinusoidal excitation magnetic field and the hysteresis loop model of the SPIOs;
S3: acquiring an original reconstructed image of FFP-MPI on the basis of an FFP moving track and a voltage signal;
S4: performing deconvolution on the original reconstructed image with respect to the PSF considering the hysteresis effect, so as to obtain a final reconstructed image.

Further, the method for acquiring the hysteresis loop of the SPIOs in S1 includes:

measuring a plurality of sets of feature point data of the SPIOs in an Alternating Current (AC) magnetic field, substituting the data into an M-H hysteresis curve model, solving to obtain parameters: saturation magnetization vector $M_s$, magnetic field coupling strength $\alpha$, magnetic domain density a, average energy k, and magnetization reversibility c, and substituting the parameters into the M-H hysteresis curve model to obtain the hysteresis loop of the SPIOs.

Further, the M-H hysteresis curve model is:

$$\begin{cases} \frac{dM}{dH} = \frac{1}{(1+c)} \frac{(M_1 - M)}{\delta k/\mu_0 - \alpha(M_1 - M)} + \frac{c}{(1+c)} \frac{dM_1}{dH} \\ M_1 = M_s \left( \coth\left(\frac{H + \alpha M}{a}\right) - \frac{a}{H + \alpha M} \right) \end{cases}$$

where, H is an externally applied excitation magnetic field, M is a magnetization vector of the SPIOs, $\mu_0$ is the permeability of vacuum; when the externally applied excitation magnetic field increases positively, $\delta=1$; when the externally applied excitation magnetic field decreases positively, $\delta=-1$.

Further, the method for calculating to obtain the PSF of the SPIOs in S2 is that:

when the SPIOs are excited by a sinusoidal excitation magnetic field, $$H(t) = A \cos(\omega t)$$

where, t is time, A is a magnetic field amplitude value, and $\omega$ is an angular frequency of an excitation magnetic field;

the above formula is substituted into the hysteresis loop model of the SPIOs to obtain a function M(t) of a magnetization vector of the SPIOs varying along with the time; a derivative of M(t) is taken with respect to the time, and the obtained PSF of the SPIOs is as follows:

$$PSF = \frac{dM(t)}{dt} = A\omega\sin(\omega t)\left(\frac{1}{(1+c)} \frac{(M_1 - M)}{\delta k/\mu_0 - \alpha(M_1 - M)} + \frac{c}{(1+c)} \frac{dM_1}{dH}\right).$$

Further, a method for acquiring an original reconstructed image of the FFP-MPI on the basis of the FFP moving track and the voltage signal in S3 includes:

moving an FFP according to a scanning track, where the moving speed is v, and the position is r; scanning the overall view field by using MPI to obtain a voltage signal u(t) of an induction coil, where a relationship between the original reconstructed image and the voltage signal is as follows:

$$IMG_{raw} = u(t)/v = c(r) *** PSF$$

where, c(r) is a variation distribution matrix of concentration along with the position, and *** is a three-dimensional convolution symbol;

dividing the voltage signal by a scanning speed, and splicing the image according to the scanning track to obtain an original reconstructed image.

Further, a method for performing deconvolution on the original reconstructed image with respect to the PSF considering the hysteresis effect to obtain a final reconstructed image in S4 is that:

$$IMG_{final} = IMG_{raw} ***PSF$$

where, *** is three-dimensional deconvolution.

The present disclosure has the following beneficial effects.

(1) By the method, starting from the hysteresis loop of the SPIOs, the PSF considering the hysteresis effect is calculated to obtain an original reconstructed image and deconvolution is performed to obtain a final reconstructed result, and an influence of the hysteresis effect of the SPIOs is added to an image reconstruction algorithm, so that the artifacts and phase errors of image reconstruction caused by the hysteresis effect of the SPIOs with large particle sizes are reduced, the deficiency in reconstruction by the traditional reconstruction method that ignores the hysteresis effect is overcome, the reconstruction speed and the resolution are greatly improved, and the reconstructed image effect is enhanced.

(2) The method has the universality for FFP-MPI devices of different structural types and different tracers. When the magnetic nanoparticles change, a new PSF can be obtained quickly by only measuring parameters in a hysteresis loop theoretical model through a Magnetic Particle Spectrometer (MPS) and changing the hysteresis loop function in theoretical calculation, so as to realize high-quality image reconstruction.

(3) The method expands the application of the SPIOs, and allows the SPIOs with larger particle sizes to be applied to the MPI, so as to increase the induced voltage and improve the detection sensitivity.

DETAILED DESCRIPTION OF THE EMBODIMENTS

The present disclosure will be further described in detail below with reference to accompanying drawings and embodiments.

A hysteresis effect-based FFP-MPI method includes the following steps.

S1: a hysteresis loop of SPIOs is acquired by measuring the parameters through an MPS and combining an M-H curve model of a hysteresis effect.

The SPIOs are excited by a high-frequency (20-45 kHz) sinusoidal excitation magnetic field in an MPI device, and a magnetization process of the SPIOs follows an M-H hysteresis curve model:

$$\begin{cases} \dfrac{dM}{dH} = \dfrac{1}{(1+c)} \dfrac{(M_1 - M)}{\delta k/\mu_0 - \alpha(M_1 - M)} + \dfrac{c}{(1+c)} \dfrac{dM_1}{dH} \\ M_1 = M_s\left(\coth\left(\dfrac{H+\alpha M}{a}\right) - \dfrac{a}{H+\alpha M}\right) \end{cases} \quad (1.1)$$

Figure 1:
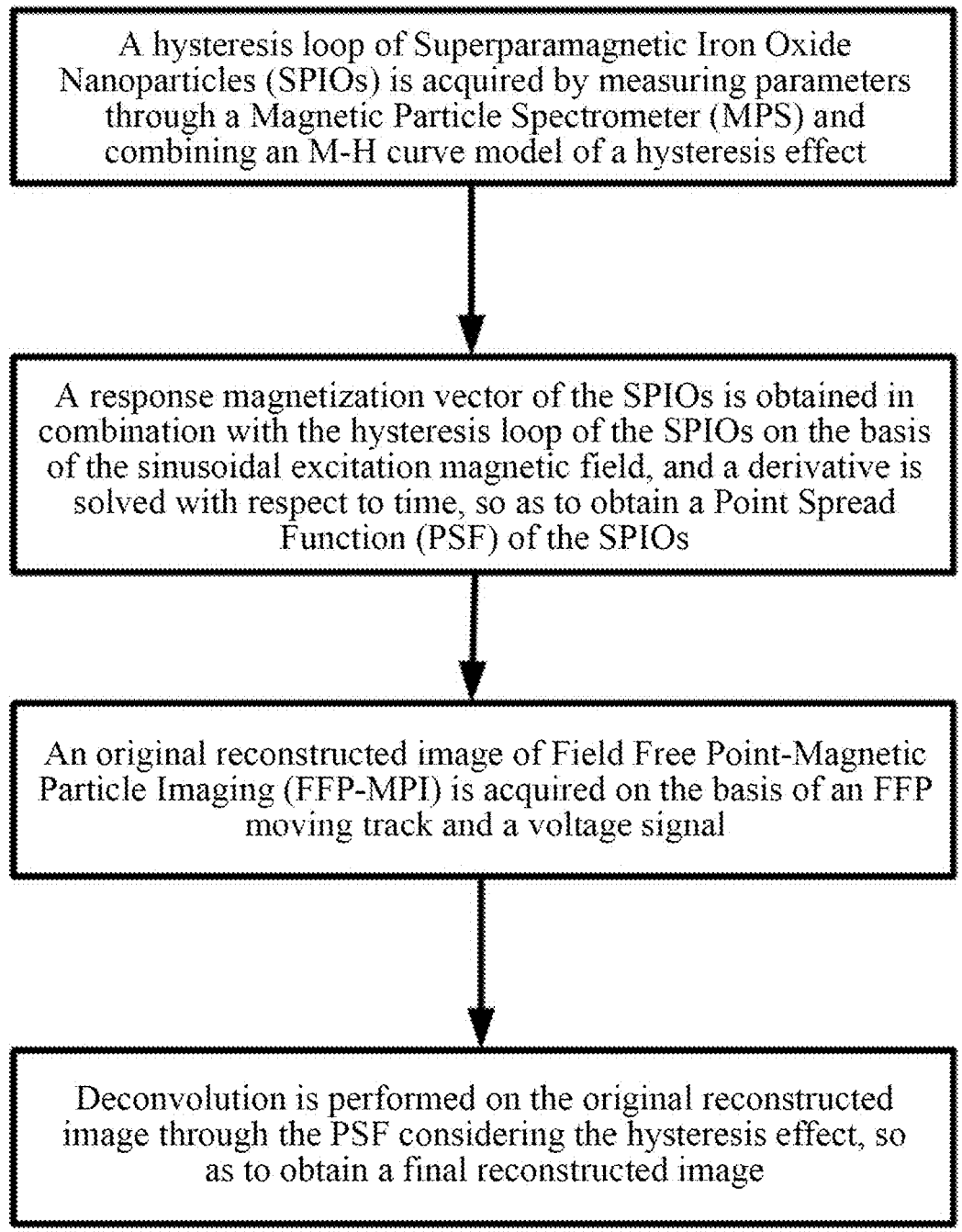
FIG. 1 illustrates a flowchart of a hysteresis effect-based FFP-MPI method.
Figure 2:
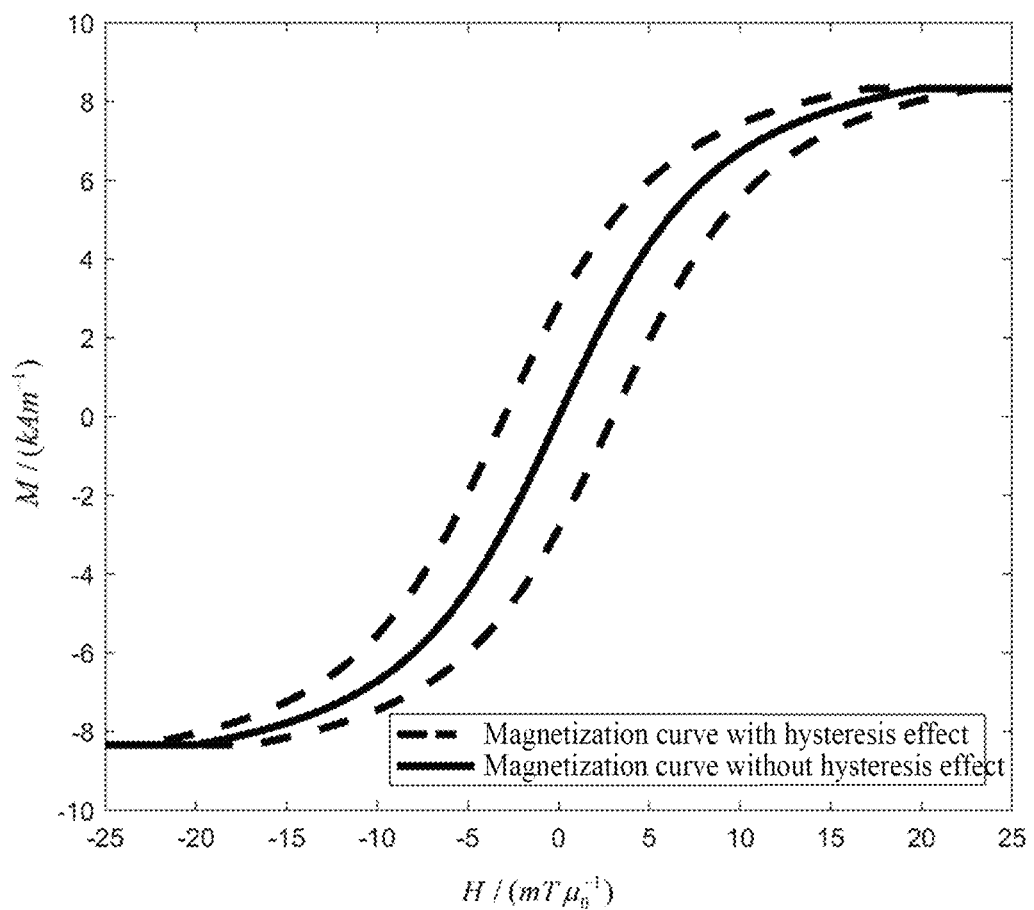
FIG. 2 illustrates an M-H hysteresis loop considering a hysteresis effect and a magnetization curve ignoring the hysteresis effect in an ideal situation.

Where, H is an externally applied excitation magnetic field, M is a magnetization vector of the SPIOs, and $\mu_0$ is the permeability of vacuum. In the model of Formula (1.1), when the externally applied excitation magnetic field increases positively, $\delta=1$; when the externally applied excitation magnetic field decreases positively, $\delta=-1$. Three sets of data of the SPIOs in an AC magnetic field can be measured through the MPS: the residual hysteresis $M_r$ when H=0, the coercive field intensity $H_c$ when M=0, and the maximum magnetization vector $M_{max}$ at the maximum magnetic field intensity $H_{max}$. The three sets of data are substituted into (1.1) to solve the following parameters: saturation magnetization vector $M_s$, magnetic field coupling strength $\alpha$, magnetic domain density a, average energy k, and magnetization reversibility c. The parameters are substituted into the M-H hysteresis curve model to obtain the hysteresis loop of the SPIOs. For example, when the diameter of the SPIOs is 30 nm, the hysteresis loop considering the hysteresis effect is shown as the hysteresis loop with the hysteresis effect in FIG. 2, and the magnetization curve not considering the hysteresis effect in an ideal situation is shown as the hysteresis curve without the hysteresis effect in FIG. 2.

S2: a response magnetization vector of the SPIOs is obtained in combination with the hysteresis loop of the SPIOs on the basis of the sinusoidal excitation magnetic field, and a derivative is solved with respect to time, so as to obtain a PSF of the SPIOs.

When the SPIOs are excited by the sinusoidal excitation magnetic field:

$$H(t)=A \cos(\omega t) \quad (1.2)$$

Figure 3:
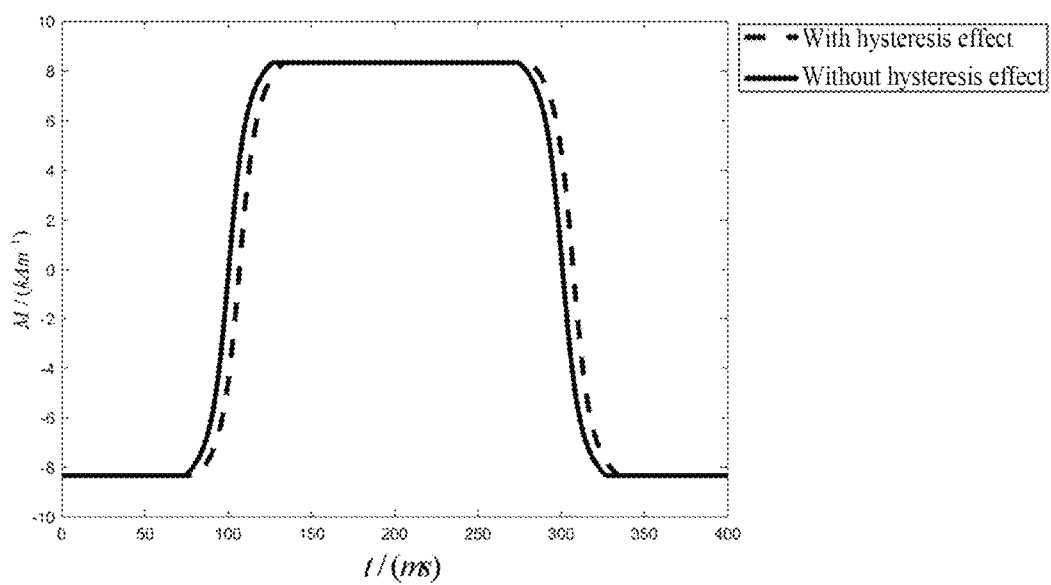
FIG. 3 illustrates magnetization vector variation curves along with time considering the hysteresis effect and ignoring the hysteresis effect in the ideal situation.

Where, t is time, A is a magnetic field amplitude value, and w is an angular frequency of an excitation magnetic field. Formula (1.2) is substituted into Formula (1.1) to obtain a function M(t) of the magnetization vector of the SPIOs along with time. As shown in FIG. 3, the variation curve of the magnetization vector considering the hysteresis effect along with time is as shown in a curve considering the hysteresis effect, and the variation of the magnetization vector ignoring the hysteresis effect in an ideal situation is shown as the curve without the hysteresis effect.

PSF is a derivative of the magnetization vector with respect to time, so:

$$PSF = \dfrac{dM(t)}{dt} = A\omega\sin(\omega t)\left(\dfrac{1}{(1+c)} \dfrac{(M_1 - M)}{\delta k/\mu_0 - \alpha(M_1 - M)} + \dfrac{c}{(1+c)} \dfrac{dM_1}{dH}\right) \quad (1.3)$$

Figure 4:
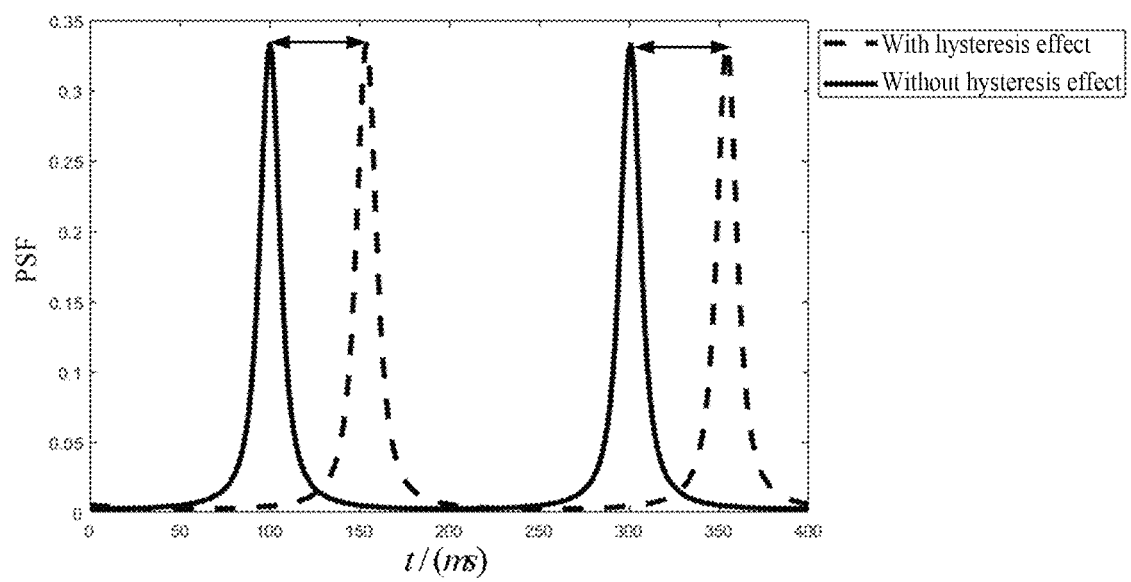
FIG. 4 illustrates PSF variation curves along with time considering the hysteresis effect and ignoring the hysteresis effect in the ideal situation.

The variation curve of PSF along with time is as shown in FIG. 4. The curve with the hysteresis effect represents the PSF considering the hysteresis effect. Compared with a hysteresis effect-free PSF ignoring the hysteresis effect, the phase moves backward, and the shapes of the two curves are the same.

S3: an original reconstructed image of the FFP-MPI is acquired on the basis of an FFP moving track and a voltage signal.

The scanning track of the FFP generally includes: a Cartesian scanning track and a Lissajous scanning track. The FFP is moved according to a certain scanning track, where the moving speed is v, and the position varying along with time is r(t); the view field of the MPI is scanned once to obtain a voltage signal u(t) of an induction coil. A relationship between the original reconstructed image and the voltage signal is as follows:

$$IMG_{raw} = u(t)/v = c(r)***PSF \quad (1.4)$$

Figure 5:
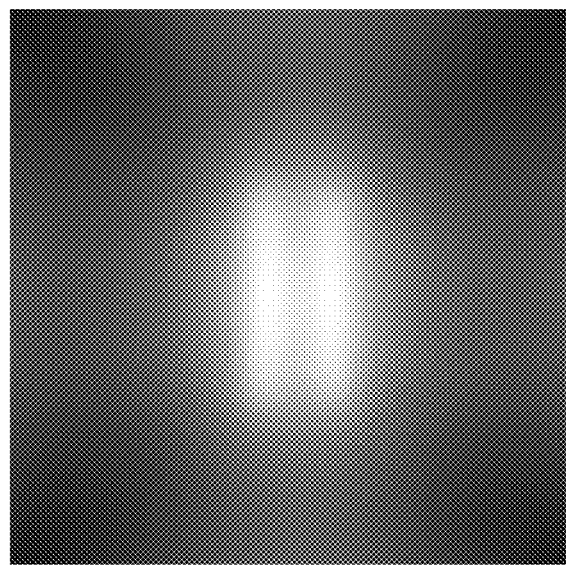
FIG. 5 illustrates an original reconstructed image of FFP-MPI.

Where, c(r) is a variation distribution matrix of concentration along with the position, and *** is a three-dimensional convolution symbol. The voltage signal is divided by a scanning speed, and the image is spliced according to the scanning track to obtain the original reconstructed image. At present, an image result used in the MPI field is the original reconstructed image. The original reconstructed image can reflect the general situation of concentration distribution of the SPIOs, but not an accurate concentration distribution result. In addition, the resolution is poor, the phase backward shift of the PSF caused by the hysteresis effect is ignored, and further image optimization is needed. For example, MPI scans two parallel strip samples, and the original reconstructed image is as shown in FIG. 5.

S4: deconvolution is performed on the original reconstructed image through the PSF considering the hysteresis effect, so as to obtain a final reconstructed image.

The original reconstructed image ignores the phase backward shift of the hysteresis effect of the SPIOs, and a position error is generated during corresponding from a time domain voltage signal to each FFP. Deconvolution is performed on the original reconstructed image with respect to the PSF, a phase backward shift error caused by the hysteresis effect is corrected by using the PSF, and the result after the deconvolution is a final reconstructed result.

$$IMG_{final} = IMG_{raw} ***PSF \quad (1.5)$$

Figure 6:
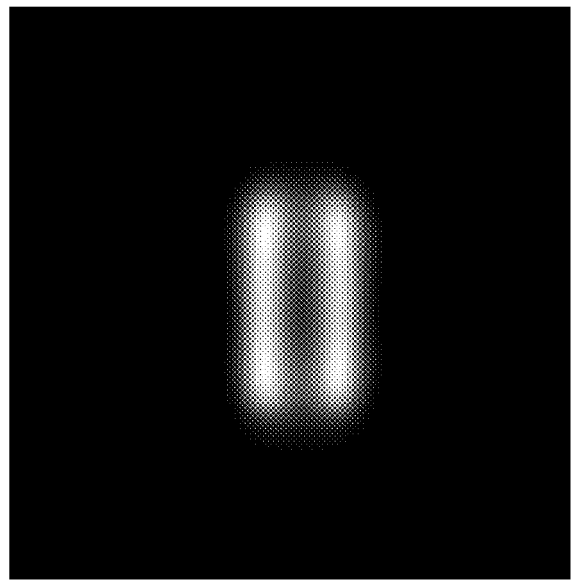
FIG. 6 illustrates a final reconstructed image of FFP-MPI.

Where, *** is three-dimensional deconvolution. For example, MPI scans two parallel strip samples, and the final reconstructed image after the deconvolution is as shown in FIG. 6.

The above is merely a specific implementation mode of the present disclosure and is not intended to limit the scope of protection of the present disclosure. Any modifications, equivalent replacements, improvements and the like made within the spirit and principle of the present disclosure shall fall within the scope of protection of the present disclosure.

The invention claimed is:

1. A hysteresis effect-based Field Free Point-Magnetic Particle Imaging (FFP-MPI) method using a Magnetic Particle Imaging (MPI) device, comprising the following steps:
S1: acquiring a hysteresis loop model of Superparamagnetic Iron Oxide Nanoparticles (SPIOs) by measuring parameters through a Magnetic Particle Spectrometer (MPS) and combining an M-H hysteresis curve model of a hysteresis effect,
wherein the SPIOs are excited by a sinusoidal excitation magnetic field in the MPI device at a frequency of 20-45 kHz, and wherein the M-H hysteresis curve model is:

$$\begin{cases} \dfrac{dM}{dH} = \dfrac{1}{(1+c)} \dfrac{(M_1 - M)}{\delta k/\mu_0 - \alpha(M_1 - M)} + \dfrac{c}{(1+c)} \dfrac{dM_1}{dH} \\ M_1 = M_s\left(\coth\left(\dfrac{H + \alpha M}{a}\right) - \dfrac{a}{H + \alpha M}\right) \end{cases};$$

S2: calculating to obtain a Point Spread Function (PSF) of the SPIOs,
wherein the step for calculating to obtain the PSF of the SPIOs further comprising:
(a) exciting the SPIOs by the sinusoidal excitation magnetic field in the MPI device, an externally applied excitation magnetic field (H) is calculated by the MPI device using formula (1.2):

$H(t) = A \cos(\omega t)$, (b) substituting the formula (1.2) into the hysteresis loop model of the SPIOs to obtain a function of a magnetization vector of the SPIOs along with the time, and
(c) obtaining the Point Spread Function (PSF) by solving a derivative of the function of the magnetization vector of the SPIOs with respect to time by using formula (1.3):

$$PSF = \dfrac{dM(t)}{dt} = A\omega\sin(\omega t)\left(\dfrac{1}{(1+c)} \dfrac{(M_1 - M)}{\delta k/\mu_0 - \alpha(M_1 - M)} + \dfrac{c}{(1+c)} \dfrac{dM_1}{dH}\right);$$

S3: acquiring an original reconstructed image of FFP-MPI on the basis of an FFP moving track and a voltage signal,
wherein the FFP moving track is obtained by moving an FFP according to a scanning track, and
wherein the scanning track includes at least one of a Cartesian scanning track and a Lissajous Scanning track; and
S4: wherein the step for performing deconvolution on the original reconstructed image with respect to the PSF considering the hysteresis effect to obtain a final reconstructed image in S4 is:

$$IMG_{final} = IMG_{raw} ***PSF,$$

wherein *** is three-dimensional deconvolution;
wherein t is time, A is a magnetic field amplitude value, ω is an angular frequency of an excitation magnetic field, c is magnetization reversibility, k is average energy, $\mu_o$ is the permeability of vacuum, α is magnetic field coupling strength, M is a magnetization vector of the SPIOs, and H is the externally applied excitation magnetic field, and when the externally applied excitation magnetic field increases, σ=1; when the externally applied excitation magnetic field decreases, σ=−1; and
performing deconvolution on the original reconstructed image of FFP-MPI with respect to the PSF considering hysteresis effect to obtain a final reconstructed image.

2. The method according to claim 1, the step for acquiring the original reconstructed image of the FFP-MPI on the basis of the FFP moving track and the voltage signal in S3 further comprising:
moving the FFP according to the scanning track, wherein a moving speed is v, and a position is r;

scanning an overall view field by using-a scanner of the MPI device to obtain the voltage signal u(t) of an induction coil,
wherein a relationship between the original reconstructed image and the voltage signal is as follows:

$$IMG_{raw} = u(t)/v = c(r) *** PSF,$$

wherein c(r) is a variation distribution matrix of a concentration of SPIOs along with the position, and *** is a three-dimensional convolution symbol; and
dividing the voltage signal by the moving speed to obtain the original reconstructed image.

\* \* \* \* \*